(12) United States Patent
Yu et al.

(10) Patent No.: US 6,660,512 B1
(45) Date of Patent: Dec. 9, 2003

(54) HUMAN LYSOZYME GENE, IT'S ENCODED POLYPEPTIDE AND THE METHOD OF PREPARING THEM

(75) Inventors: Long Yu, Shanghai (CN); Qiang Fu, Shanghai (CN); Yong Zhao, Shanghai (CN); Honglai Zhang, Shanghai (CN); Anding Bi, Shanghai (CN)

(73) Assignee: Yu Long, Shanghai (CN)

( * ) Notice: Subject to any disclaimer, the term of this patent is extended or adjusted under 35 U.S.C. 154(b) by 0 days.

(21) Appl. No.: 09/786,025

(22) PCT Filed: Aug. 30, 1999

(86) PCT No.: PCT/CN99/00133

§ 371 (c)(1),
(2), (4) Date: Jun. 8, 2001

(87) PCT Pub. No.: WO00/12717

PCT Pub. Date: Mar. 9, 2000

(30) Foreign Application Priority Data

Aug. 31, 1998 (CN) .......................................... 98111044 A

(51) Int. Cl.$^7$ ............................ C12N 9/36; C12N 15/56
(52) U.S. Cl. ..................... 435/206; 435/200; 435/320.1; 435/252.3; 435/252.33; 435/69.1; 435/71.1; 435/325; 536/23.2; 536/23.5
(58) Field of Search ................................ 435/206, 200, 435/320.1, 252.3, 252.33, 69.1, 71.1, 325; 536/23.2, 23.5

(56) References Cited

FOREIGN PATENT DOCUMENTS

WO         WO99/09155      *   2/1999   ........... C12N/15/11

OTHER PUBLICATIONS

Brewer LA, Duan R et al, Human secreted protein, cDNA fragment containing gene 36. Feb. 1999 Alignment SEQ ID No.: 3.*
Brewer LA, Duan R et al, Human secreted protein fragment encoded from gene 36. Feb. 1999 Alignment with SEQ ID No.: 4.*
Strausberg R. NCI, Cancer Genome Anatomy Project (CGAP), Tumor Gene Index Dec. 1998, Alignment with SEQ ID No.: 3.*
NCI–GAP National Cancer Inst, Cancer Genome Anatomy Project http://www.ncbi.nlm.nih.gov/ncicgap Dec. 31, 1998 EMBL Acc# AA812577 Alignment with SEQ ID No.: 4.*
Agric Biol Chem 1991, Jul.;55(7):1707–13 The amino acid sequence of reeves' pheasant (syrmaticus reevesii) Lysozyme.
Acta Otolaryngol (Stockh) Nov. 1997; 117(6):851–855. "The effects of oxymetazoline on Lysozyme secretion from the human nasal mucosa".
Yajima et al. vol. 26, Issue 4 (1988). pp. 373–395. CRC Clinical Reviews in Food Science and Nutrition.

Anticancer Research 9: 583–592 (1989) Lysozyme and Cancer: Role of Exogenous Lysozyme as Anticancer Agent (Review) by Sava et al.
Lubbert M. Henschler R, Kreutz M, Andreesen R. Mertelsmann R, Herrmann F, "The human lysozyme gene undergoes stepwise demethylation during phagocyte maturation" *Leukmia* Jul. 1997: 11(7):990 (Abstract).
Mendeluk GR, Blanco AM, Bregni C, "Viscosity of human seminal fluid: role of lysomzyme" *Arch Androl* Jan.–Feb. 1997;38(1):7 (Abstract).
Bentley GA, "The crystal structures of complexes formed between lysozyme and antibody fragments" *EXS* 1996;75:301 (Abstract).
Dupont C, Kluepfel D, Morosoli R, "Evidence for lysozyme–type mechanism of hydrolysis in xylanases" *EXS* 1996;75:411 (Abstract).
Fischer B, "Folding of lysozyme" *EXS* 1996:75:143 (Abstract).
Holtje JV, "Lysozyme substrates" *EXS* 1996; 75:105 (Abstract).
Imoto T, "Engineering of lysozyme" *EXS* 1996;75:163 (Abstract).
Irwin DM, Yu M, Wen Y, "Isolation and characterization of vertebrate lysozyme genes" *EXS* 1996;75:225 (Abstract).
Karplus M, Post CB, "Simulations of lysozyme: internal motions and the reaction mechanism" *EXS* 1996;75:111 (Abstract).
Prager EM, "Adaptive evolution of lysozyme: changes in amino acid sequence, regulation of expression and gene mumber" *EXS* 1996;75:323 (Abstract).
Short ML, Nickel J. Schmitz A, Renkawitz R, "Lysozyme gene expression and regulation" *EXS* 1996;75:243 (Abstract).
Wang YB, "Antibacterial mechanisms of lysozyme on Streptococcus mutans" *Zhonghua Ya Yi Xue Hui Za Zhi* Sep. 1990;9(3):87 (Abstract).
Chung LP, Keshav S, Gordon S, "Cloning the human lysozyme cDNA: inverted Alu repeat in the mRNA and in situ hybridization for macrophages and Paneth cells" *Proc Natl Acad Sci USA* Sep. 1988;85(17):6227 (Abstract).
Castanon MJ, Spevak W, Adolf GR, Chlebowicz–Sledziewska E, Sledziewski A, "Cloning of human lysozyme gene and expression in the yeast *Saccharomyces cerevisiae*" *Gene* Jun. 30, 1998;66(2):223 (Abstract).
Saedi MS, Garvey KJ, Ito J, "Cloning and purification of a unique lysozyme produced by Bacillus phage phi 29" *Proc Natl Acad Sci USA* Feb. 1987;84(4):955 (Abstract).

(List continued on next page.)

*Primary Examiner*—Rebecca E. Prouty
*Assistant Examiner*—Sheridan L Swope
(74) *Attorney, Agent, or Firm*—Baker Botts L.L.P.

(57) ABSTRACT

The invention relates to LYC4, a novel member of the lysozyme gene family. The invention provides the cDNA sequence encoding the novel lysozyme, the polypeptide encoded by the sequence, as well as methods for producing said novel human lysozyme utilizing recombinant technology. The invention also provides the use of the novel human lysozyme.

12 Claims, 1 Drawing Sheet

OTHER PUBLICATIONS

Rennell D, Poteete AR, "Phage P22 lysis genes: nucleotide sequences and functional relationships with T4 and lambda genes" *Virology* May 1985;143(1):280 (Abstract).

Owen JE, Schultz DW, Taylor A, Smith GR, "Nucleotide sequence of the lysozyme gene of bacteriophage T4 Analysis of mutations involving repeated sequences" *J Mol Biol* Apr. 5, 1983;165(2):229 (Abstract).

Jung A, Sippel AE, Grez M, Schutz G, "Exons encode functional and structural units of chicken lysozyme" *Proc Natl Acad Sci USA* Oct. 1980;77(10):5759 (Abstract).

Reitamo S, Klockars M, Adinolfi M, Osserman EF, "Human lysozyme (origin and distribution in health and disease)" *Ric Clin Lab* Oct.–Dec. 1978;8(4):211 (Abstract).

Araki T, Kuramoto M, Torikata T, 1991, "The amino acid sequence of reeves' pheasant (Syrmaticus reevesii) lysozyme" Agric Biol Chem. Jul.;55(7):1707–1713.

Browning S, Housley D, Richards R, Eccles R, 1997, "The effects of oxymetazoline on lysozyme secretion from the human nasal mucosa" Acta Otolaryngol (Stockh) Nov.;117(6):851–855.

Proctor VA, Cunningham FE, 1988, "The Chemistry of lysozyme nad its use as a food preservative and pharmaceutical" CRC Critical Reviews in Food Science and Nutrition, 26(4);373 395.

Sava G, Benetti A, Ceschia V, Pacor S, 1989, "Lysozyme and cancer: role of exogenous lysozyme as anticancer agent (review)" Anticnacer Res May–Jun.;9(3):583–591.

\* cited by examiner

```
            10        20        30        40        50        60
LYC4     MKASVVLSLLGYLVVPSGAYILGRCTVAKKLHDGGLDYFEGYSLENWVCLAYFESKFNPM
                          . ::: .:  ..   :::  ..:::: ::::  :  :::.::
sp|P24533 K------------------VYGRCELAAAMKRLGLDNYRGYSLGNWVCAAKFESNFNTH
                              10        20        30        40

70        80        90       100       110
LYC4     AIYENTREGYTGFGLFQMRGSDWCGDH----GRNRCHMSCSALLNPNLEKTIKCAKTIVK
         : .:: .: : .:..:. .   ::.:      .:: ::.:::::.  ...::: ::.
sp|P24533 ATNRNT-DGSTDYGILQINSRWWCNDGRTPGSRNLCHISCSALLSSDITASVNCAKKIVS
             50        60        70        80        90       100

120       130       140
LYC4     GKEGMGAWPTWSRYCQYSDTLARWLDGCKL
         ..::.::  .:   :. .:.  :  :.  :
sp|P24533 DRNGMNAWVAWRNRCKGTDVNA-WIRGCRL
            110       120
```

Fig. 1A

```
            10        20        30        40        50        60
LYC4     MKASVVLSLLGYLVVPSGAYILGRCTVAKKLHDGGLDYFEGYSLENWVCLAYFESKFNPM
                :         . ::: .:  ..   :::  ..:::: ::::  :  :::.::
sp|P49663 GK------------------VYGRCELAAAMKRMGLDNYRGYSLGNWVCAAKFESNFNTG
                              10        20        30        40

70        80        90       100       110
LYC4     AIYENTREGYTGFGLFQMRGSDWCGDHGR-----NRCHMSCSALLNPNLEKTIKCAKTIV
         : .:: .: : .:..:. .   ::.: ::      : ::. ::::: ..  ...::: ::
sp|P49663 ATNRNT-DGSTDYGILQINSRWWCND-GRTPGSKNLCHIPCSALLSSDITASVNCAKKIV
             50        60        70        80        90       100

120       130       140
LYC4     KGKEGMGAWPTWSRYCQYSDTLARWLDGCKL
         .  .::.:: .:   :. .:.  :. :::.:
sp|P49663 SDGDGMNAWVAWRKHCKGTD-VNVWIRGCRL
               110       120       130
```

Fig. 1B

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 1
cacacgtcga agctgctgca gtg                                          23

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 2
catcctgcat ccccggatga agc                                          23

<210> SEQ ID NO 3
<211> LENGTH: 775
<212> TYPE: DNA
<213> ORGANISM: Human
<220> FEATURE:
<221> NAME/KEY: CDS
```

<222> LOCATION: (179)...(619)
<223> OTHER INFORMATION: Lysozyme LYC4

<400> SEQUENCE: 3

```
cacacgtcga agctgctgca gtggctgttc ttccctccc cttggaaagg caccaaaagc      60
cagcctttgg aagggctggt ggactgtgcc cttctttccc ttcagagaac cagtgtccct    120
gtgactccac ccactcatct ggccaccgtt gccctgacct gccaggagcc tggagaag     178
```

| | | | | | | | | | | | | | | | | |
|---|---|---|---|---|---|---|---|---|---|---|---|---|---|---|---|---|
| atg | aag | gca | tcc | gtg | gtt | ctc | tcc | ctc | ctt | ggc | tac | ctg | gtg | gtt | cca | 226 |
| Met | Lys | Ala | Ser | Val | Val | Leu | Ser | Leu | Leu | Gly | Tyr | Leu | Val | Val | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agt | ggt | gct | tac | atc | ttg | ggg | cgt | tgc | aca | gtg | gct | aag | aaa | ctc | cac | 274 |
| Ser | Gly | Ala | Tyr | Ile | Leu | Gly | Arg | Cys | Thr | Val | Ala | Lys | Lys | Leu | His | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gga | ggc | ctg | gat | tat | ttt | gag | ggc | tat | agc | ctt | gag | aac | tgg | gtg | 322 |
| Asp | Gly | Gly | Leu | Asp | Tyr | Phe | Glu | Gly | Tyr | Ser | Leu | Glu | Asn | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| tgc | ctg | gcc | tac | ttt | gag | agc | aag | ttc | aac | ccc | atg | gcc | atc | tac | gag | 370 |
| Cys | Leu | Ala | Tyr | Phe | Glu | Ser | Lys | Phe | Asn | Pro | Met | Ala | Ile | Tyr | Glu | |
| 50 | | | | | 55 | | | | | 60 | | | | | | |

| | | | | | | | | | | | | | | | | |
|---|---|---|---|---|---|---|---|---|---|---|---|---|---|---|---|---|
| aac | aca | cgt | gag | ggc | tac | act | ggc | ttt | ggc | ctc | ttt | cag | atg | cgt | ggc | 418 |
| Asn | Thr | Arg | Glu | Gly | Tyr | Thr | Gly | Phe | Gly | Leu | Phe | Gln | Met | Arg | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agt | gac | tgg | tgt | ggc | gac | cat | ggc | agg | aac | cgc | tgc | cat | atg | tca | tgt | 466 |
| Ser | Asp | Trp | Cys | Gly | Asp | His | Gly | Arg | Asn | Arg | Cys | His | Met | Ser | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| tcc | gct | tta | ctg | aat | cct | aat | tta | gag | aag | aca | att | aaa | tgt | gcc | aag | 514 |
| Ser | Ala | Leu | Leu | Asn | Pro | Asn | Leu | Glu | Lys | Thr | Ile | Lys | Cys | Ala | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| acc | att | gta | aaa | gga | aaa | gaa | ggg | atg | gga | gca | tgg | ccc | acc | tgg | tcc | 562 |
| Thr | Ile | Val | Lys | Gly | Lys | Glu | Gly | Met | Gly | Ala | Trp | Pro | Thr | Trp | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| cgg | tac | tgc | cag | tac | tcc | gat | acc | ctg | gca | cgg | tgg | ctg | gat | ggt | tgc | 610 |
| Arg | Tyr | Cys | Gln | Tyr | Ser | Asp | Thr | Leu | Ala | Arg | Trp | Leu | Asp | Gly | Cys | |
| | 130 | | | | | 135 | | | | | 140 | | | | | |

| | | | | | | |
|---|---|---|---|---|---|---|
| aag | ctg | tag | ccgcctgcat | ggccctgca | gcactcacca | gttgcatctt | 659 |
| Lys | Leu | * | | | | |
| 145 | | | | | | |

```
gtgaatgaag gtgcttttct gcttgctgct tcagtcaatc cttttgatga tctcaccact    719
ttaagagttc cagatggaaa aagacaaaag tttgcttcat ccggggatgc aggatg       775
```

<210> SEQ ID NO 4
<211> LENGTH: 146
<212> TYPE: PRT
<213> ORGANISM: Human

<400> SEQUENCE: 4

```
Met Lys Ala Ser Val Val Leu Ser Leu Leu Gly Tyr Leu Val Val Pro
1               5                   10                  15

Ser Gly Ala Tyr Ile Leu Gly Arg Cys Thr Val Ala Lys Lys Leu His
            20                  25                  30

Asp Gly Gly Leu Asp Tyr Phe Glu Gly Tyr Ser Leu Glu Asn Trp Val
        35                  40                  45

Cys Leu Ala Tyr Phe Glu Ser Lys Phe Asn Pro Met Ala Ile Tyr Glu
    50                  55                  60

Asn Thr Arg Glu Gly Tyr Thr Gly Phe Gly Leu Phe Gln Met Arg Gly
65                  70                  75                  80

Ser Asp Trp Cys Gly Asp His Gly Arg Asn Arg Cys His Met Ser Cys
```

-continued

```
                85                  90                  95
Ser Ala Leu Leu Asn Pro Asn Leu Glu Lys Thr Ile Lys Cys Ala Lys
            100                 105                 110
Thr Ile Val Lys Gly Lys Glu Gly Met Gly Ala Trp Pro Thr Trp Ser
        115                 120                 125
Arg Tyr Cys Gln Tyr Ser Asp Thr Leu Ala Arg Trp Leu Asp Gly Cys
    130                 135                 140
Lys Leu
145
```

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 5
ttgcggatcc atgaaggcat ccgtggttc                          29

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 6
gttcgtcgac ctacagcttg caaccatcc                          29

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 7
ttgcaagctt atgaaggcat ccgtggttc                          29

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 8
gttcggatcc ctacagcttg caaccatcc                          29

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 9
ttgcaagctt tacatcttgg ggcgttg                            27

<210> SEQ ID NO 10
<211> LENGTH: 19
<212> TYPE: PRT
<213> ORGANISM: Artificial Sequence

```
<220> FEATURE:
<223> OTHER INFORMATION: Signature sequence of lysozyme and
      alpha-lactoalbumin
<221> NAME/KEY: VARIANT
<222> LOCATION: (2)...(4)
<223> OTHER INFORMATION: Any amino acid
<221> NAME/KEY: VARIANT
<222> LOCATION: (6)...(7)
<223> OTHER INFORMATION: Any amino acid
<221> NAME/KEY: VARIANT
<222> LOCATION: (8)...(8)
<223> OTHER INFORMATION: Leucine, methionine, or phenylalanine
<221> NAME/KEY: VARIANT
<222> LOCATION: (9)...(11)
<223> OTHER INFORMATION: Any amino acid
<221> NAME/KEY: VARIANT
<222> LOCATION: (12)...(12)
<223> OTHER INFORMATION: Aspartate, glutamate, or asparagine
<221> NAME/KEY: VARIANT
<222> LOCATION: (13)...(13)
<223> OTHER INFORMATION: Leucine or isoleucine
<221> NAME/KEY: VARIANT
<222> LOCATION: (14)...(18)
<223> OTHER INFORMATION: Any amino acid

<400> SEQUENCE: 10

Cys Xaa Xaa Xaa Cys Xaa Xaa Xaa Xaa Xaa Xaa Xaa Xaa Xaa
 1               5                  10                  15

Xaa Xaa Cys

<210> SEQ ID NO 11
<211> LENGTH: 129
<212> TYPE: PRT
<213> ORGANISM: Reeve's pheasant

<400> SEQUENCE: 11

Lys Val Tyr Gly Arg Cys Glu Leu Ala Ala Ala Met Lys Arg Leu Gly
 1               5                  10                  15

Leu Asp Asn Tyr Arg Gly Tyr Ser Leu Gly Asn Trp Val Cys Ala Ala
                20                  25                  30

Lys Phe Glu Ser Asn Phe Asn Thr His Ala Thr Asn Arg Asn Thr Asp
            35                  40                  45

Gly Ser Thr Asp Tyr Gly Ile Leu Gln Ile Asn Ser Arg Trp Trp Cys
50                  55                  60

Asn Asp Gly Arg Thr Pro Gly Ser Arg Asn Leu Cys His Ile Ser Cys
65                  70                  75                  80

Ser Ala Leu Leu Ser Ser Asp Ile Thr Ala Ser Val Asn Cys Ala Lys
                85                  90                  95

Lys Ile Val Ser Asp Arg Asn Gly Met Asn Ala Trp Val Ala Trp Arg
            100                 105                 110

Asn Arg Cys Lys Gly Thr Asp Val Asn Ala Trp Ile Arg Gly Cys Arg
        115                 120                 125

Leu

<210> SEQ ID NO 12
<211> LENGTH: 130
<212> TYPE: PRT
<213> ORGANISM: Green pheasant

<400> SEQUENCE: 12

Gly Lys Val Tyr Gly Arg Cys Glu Leu Ala Ala Ala Met Lys Arg Met
 1               5                  10                  15

Gly Leu Asp Asn Tyr Arg Gly Tyr Ser Leu Gly Asn Trp Val Cys Ala
                20                  25                  30
```

-continued

```
Ala Lys Phe Glu Ser Asn Phe Asn Thr Gly Ala Thr Asn Arg Asn Thr
        35                  40                  45

Asp Gly Ser Thr Asp Tyr Gly Ile Leu Gln Ile Asn Ser Arg Trp Trp
    50                  55                  60

Cys Asn Asp Gly Arg Thr Pro Gly Ser Lys Asn Leu Cys His Ile Pro
65                  70                  75                  80

Cys Ser Ala Leu Leu Ser Ser Asp Ile Thr Ala Ser Val Asn Cys Ala
            85                  90                  95

Lys Lys Ile Val Ser Asp Gly Asp Gly Met Asn Ala Trp Val Ala Trp
            100                 105                 110

Arg Lys His Cys Lys Gly Thr Asp Val Asn Val Trp Ile Arg Gly Cys
        115                 120                 125

Arg Leu
    130
```

HUMAN LYSOZYME GENE, IT'S ENCODED POLYPEPTIDE AND THE METHOD OF PREPARING THEM

The invention relates to a new polynucleotide, the polypeptide encoded by said polynucleotide, the uses of said polynucleotide and polypeptide, and the methods for preparing same. In particular, the polypeptide of the invention is identified as a new member of the lysozyme family.

Lysozyme exists ubiquitously in all parts of organisms, including various tissues, organs, and sera; it is especially abundant in egg white. Lysozyme is mainly secreted by the epithelial cell of certain glands and some kinds of leukocyte.

Lysozyme was first reported by Fleming, et al. in 1922. Afterward, lysozyme has been widely studied. A lot of papers concerning its crystal structure, protein catalytic domains, catalytic dynamics, immunology, molecular evolutionary, and so on, have been published. Lysozyme is one of the proteins that are studied most extensively and intensively. However, the study on lysozyme gene is not yet sufficient. Nowadays, only a few lysozyme genes from different species, such as E.coli T4, salmonella P22 phage, bacillus φ phage and chicken, etc., have been cloned. (1983 J. Mol. Biol. 165. 229–248; 1985 Virology 143, 280–289; 1987 Proc. Natl. Acad. Sci. USA, 77, 5759–5763). The cloning about human lysozyme gene was also reported (1988, Gene 66,223–234).

The main function of lysozyme is to hydrolyze the beta(1–4) glycosidic bond between N-acetylmuramic acid (NAM) and N-acetylgluconic acid (NAG) of the bacterial cell wall. In the organism, lysozyme can act as a nonspecific immune molecule against bacterial infections, and as a digestive enzyme in enteron and some mollusks which live on bacteria. Further, lysozyme has the function of inhibiting tumor growth. Therefore, lysozyme has important applications in both industry and medicine.

One purpose of the invention is to provide a new polynucleotide which encodes a new member of lysozyme gene family. The new human lysozyme is named LYC4.

Another purpose of the invention is to provide a new member of lysozyme protein family, which is named LYC4.

Still another purpose of the invention is to provide a new method for preparing said new human lysozyme by recombinant techniques.

The invention also relates to the uses of said human lysozyme and its coding sequence.

In one aspect, the invention provides an isolated DNA molecule, which comprises a nucleotide sequence encoding a polypeptide having human LYC4 protein activity, wherein said nucleotide sequence shares at least 70% homology to the nucleotide sequence of nucleotides 179–619 in SEQ ID NO:3, or said nucleotide sequence can hybridize to the nucleotide sequence of nucleotides 179–619 in SEQ ID NO:3 under moderate stringency. Preferably, said nucleotide sequence encodes a polypeptide comprising the amino acid sequence of SEQ ID NO:4, more preferably, said sequence comprises the sequence shown in SEQ ID NO:4.

Further, the invention provides an isolated LYC4 polypeptide, which comprises a polypeptide having the amino acid sequence of SEQ ID NO:4, its active fragments, and its active derivatives. Preferably, the polypeptide is a polypeptide having the amino acid sequence of SEQ ID NO:4.

The invention also provides a vector comprising said isolated DNA.

The invention further provides a host cell transformed with said vector.

In another aspect, the invention provides a method for producing a polypeptide with the activity of LYC4 protein, which comprises:
(a) forming an expression vector of LYC4 protein comprising the nucleotide sequence encoding the polypeptide having the activity of LYC4 protein, wherein said nucleotide sequence is operably linked with an expression regulatory sequences, and said nucleotide sequence shares at least 70% homology to the nucleotide sequence of positions 179–619 in SEQ ID NO:3;
(b) introducing the vector of step (a) into a host cell, thereby forming a recombinant cell of LYC4 protein;
(c) culturing the recombinant cell of step (b) under the conditions suitable for the expression of LYC4 polypeptides;
(d) isolating the polypeptides having the activity of LYC4 protein.

In one embodiment of the present invention, the isolated polynucleotide has a full length of 775 nucleotides, whose detailed sequence is shown in SEQ ID NO:3. The open reading frame (ORF) locates at nucleotides 179–619.

In the present invention, the term "isolated" or "purified" or "substantially pure" DNA refers to a DNA or fragment which has been isolated from the sequences which frank it in a naturally occurring state. The term also applied to DNA or DNA fragment which has been isolated from other components naturally accompanying the nucleic acid and from proteins naturally accompanying it in the cell.

In the present invention, the term "LYC4 protein encoding sequence" or "LYC4 polypeptide encoding sequence" refers to a nucleotide sequence encoding a polypeptide having the activity of LYC4 protein, such as the nucleotide sequence of positions 179–619 in SEQ ID NO:3 or its degenerate sequence. The degenerate sequences refer to the sequences formed by replacing one or more codons in the ORF of 179–619 in SEQ ID NO:3 with degenerate codes which encode the same amino acid. Because of the degeneracy of codon, the sequence having a homology as low as about 70% to the sequence of nucleotides 179–619 in SEQ ID NO:3 can also encode the sequence shown in SEQ ID NO:4. The term also refers to the nucleotide sequences that hybridize with the nucleotide sequence of nucleotides 179–619 in SEQ ID NO:3 under moderate stringency or preferably under high stringency. In addition, the term also refers to the sequences having a homology at least 70%, preferably 80%, more preferably 90% to the nucleotide sequence of nucleotides 179–619 in SEQ ID NO:3.

The term also refers to variants of the sequence in SEQ ID NO:3, which are capable of coding for a protein having the same function as human LYC4 protein. These variants includes, but are not limited to: deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "LYC4 polypeptide" or "LYC4 protein" refers to a polypeptide having the activity of LYC4 protein comprising the amino acid sequence of SEQ ID NO:4. The term also comprises the variants of said amino acid sequence which have the same function of human lysozyme. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein function are usually unchanged when an amino residue is substituted by a similar or analogous one. Further, the addition of one or several amino acids at C-terminal and/or N-terminal will not change the function of protein. The term also includes the active fragments and derivatives of LYC4 protein.

The variants of polypeptide include homologous sequences, allelic variants, natural mutants, induced mutants, proteins encoded by DNA which hybridizes to LYC4 DNA under high or low stringency conditions as well as the polypeptides or proteins retrieved by antisera raised against LYC4 polypeptide. The present invention also provides other polypeptides, e.g., fusion proteins, which include the LYC4 polypeptide or fragments thereof. In addition to substantially full-length polypeptide, the soluble fragments of LYC4 polypeptide are also provided. Generally, these fragments comprise at least 10, typically at least 30, preferably at least 50, more preferably at least 80, most preferably at least 100 consecutive amino acids of human LYC4 polypeptide.

The present invention also provides the analogues of LYC4 protein or polypeptide. Analogues can differ from naturally occurring LYC4 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding LYC4 polypeptide. Said antisense sequence can be used to inhibit expression of LYC4 in cells.

The invention also include probes, typically having 8–100, preferably 15–50 consecutive nucleotides. These probes can be used to detect the presence of nucleic acid molecules coding for LYC4 in samples.

The present invention also includes methods for detecting LYC4 nucleotide sequences, which comprises hybridizing said probes to samples, and detecting the binding of the probes. Preferably, the samples are products of PCR amplification. The primers in PCR amplification correspond to coding sequence of LYC4 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by LYC4 DNA or fragments thereof. By "specificity" is meant an antibody which binds to the LYC4 gene products or a fragments thereof. Preferably, the antibody binds to the LYC4 gene products or a fragments thereof and does not substantially recognize and bind to other antigenically unrelated molecules. Antibodies which bind to LYC4 and block LYC4 protein and those which do not affect the LYC4 function are included in the invention. The invention also includes antibodies which bind to the LYC4 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified LYC4 gene products, or its antigenic fragments can be administrated to animals to induce the production of polyclonal antibodies. Similarly, cells expressing LYC4 or its antigenic fragments can be used to immunize animals to produce antibodies. Antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block LYC4 function and those which do not affect LYC4 function. Antibodies in the invention can be produced by routine immunology techniques and using fragments or functional regions of LYC4 gene product. These fragments and functional regions can be prepared by recombinant methods or synthesized by a polypeptide synthesizer. Antibodies binding to unmodified LYC4 gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

In one embodiment, the polynucleotide of the invention is 775 bp in full length whose detailed sequence is shown in SEQ ID NO:3 with the ORF located at positions 179–619. Said polynucleotide was obtained as follows: human brain λ gt 11 cDNA library (Clontech) was used as a template and PCR was carried out with the synthetic forward primer A1:

5'-CACACGTCGAAGCTGCTGCAGTG-3' and reverse primer B1 :5'-CATCCTGCATCCCCGGATGAAGC-3'. A target fragment of 775 bp was obtained. The sequencing of the PCR product gave the full length cDNA sequence shown in SEQ ID NO:3.

Homology comparison showed that the nucleotide sequence and the coded protein sequence of the invention shared remarkable homology to other lysozymes from different origins. Therefore, it indicates it is a new member of lysozyme family and has some important functions of the family.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria. Further, lysozyme has the function of inhibiting tumor growth. In 1955, Caselli and Shumacher (Boll Ocul 34:513–533, 1955) reported on the lysozyme-mediated 70% inhibition of neoplastic transformation in cornea of chicken infected by Rous sarcoma virus. Many other experiments indicated that lysozyme participates in the process of tumor diffusion and interacts with phospho- and glucolipid molecule of tumor cells. The inhibition effect on human tumor of lysozyme was reported and patented (1980 Jpn Kokai, Tokkyo Koho 33,409; 1980 Jpn Kokai Tokkyo Koho 33,408). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

The Cloning and Sequencing of LYC4 cDNA Sequence

1. Amplification with Primers

The template was human brain λ gt 11 cDNA library (commercially available from Clontech). PCR with forward primer A1: 5'-CACACGTCGAAGCTGCTGCAGTG-3' (SEQ ID NO:1) and reverse primer B1 :5'-CATCCTGCATCCCCGGATGAAGC-3' (SEQ ID NO:2) was carried out. The PCR condition for A1/B was 4 mins at 93° C.; followed by 35 cycles with 1 min at 93° C., 1 min at 70° C., and 1 min at 72° C.; and, finally 5 mins at 72° C. The PCR fragments were detected by electrophoresis. The target fragment was 775 bp.

2. Sequencing PCR Products

The obtained PCR products were linked with pGEM-T® vector (Promega) and transformed into E. coli JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 775 bp was obtained by overlapping the sequences with computer software. The detailed sequence is shown in SEQ ID NO:3 with an open reading frame (ORF) located at nucleotides 179–619.

According to the resultant full-length cDNA sequence, the amino acid sequence of LYC4 was deduced, having 146 amino acid residues totally. See SEQ ID NO:4 for its amino acid sequence in details.

EXAMPLE 2

Homologous Comparison

In one embodiment, the polynucleotide of the invention is 775 bp in full length whose detailed sequence is shown in SEQ ID NO:3 with the ORF located at positions 179–619. Said polynucleotide was obtained as follows: human brain gt 11 cDNA library (Clontech) was used as a template and PCR was carried out with the synthetic forward primer A1 5'-CACACGTCGAAGCTGCTGCAGTG-3' (SEQ ID NO. 1) and reverse primer B1: 5'-CATCCTGCATCCCCGGATGAAGC-3' (SEQ ID NO. 2). A target fragment of 775 bp was obtained. The sequencing of the PCR product gave the full length cDNA sequence shown in SEQ ID NO:3.

In particular, in amino acid sequence of LYC4, there exists a 19 amino acids.signature sequence of lysozyme and alpha-lactoalbumin: $CX_3CX_2(L/M/F)X_3(D/E/N)(L/I)X_5C$ [Note: In the sequence, X represents any amino acid, digits such as "2" denote the number of amino acid, "(L/M/H)" represents any of these three amino acids]. Lysozyme and alpha-lactoalbumin are two proteins related closely in evolution (Eur. J. Biochem. 182: 111–118). In the protein of the present invention, the sequence matching the signature is: CHMSCSALLNPNLEKTIKC(residues 92–110 in SEQ ID NO:4). It indicates that the LYC4 of the present invention belongs to lysozyme family, and has the relative functions of the lysozyme family.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria.

Lysozyme has important applications in both industry and medicine.

First, in industry (mainly in food industry), lysozyme can be used as a preservative or additive for food. In this respect, the Japanese have developed many use of lysozyme and owe many patents. For example, they use lysozyme as a preservative for fresh fruit, vegetable, soybean milk, marine foods and meat. Lysozyme can also be used as an additive for infant's foods to simulate human milk (1988, Crit Rev Food Sci Nutr 26(4):359–395).

FIG. 1 shows an alignment comparison of amino acid sequences of human LYC4 and other lysozymes. FIG. 1A shows a homology comparison of amino acid sequences of human LYC4 (SEQ ID NO. 4) and lysozyme C of Reeves's pheasant (sp|p24533) (SEQ ID NO. 11). FIG. 1B shows a homology comparison of amino acid sequences of human LYC4 (SEQ ID NO. 4) and lysozyme C of green pheasant (sp|p49663) (SEQ ID NO. 12). The identical amino acids are indicated by ":" between the sequences, and the similar amino acids indicated by ".". The similar amino acids are as follows: A,S,T; D,E; N,Q; R,K; I,L,M,V; F,Y,W.

Further, lysozyme has the function of inhibiting tumor growth. In 1955, Caselli and Shumacher (1955, Boll Ocul 34:513–533) reported on the lysozyme-mediated 70% inhibition of neoplastic transformation in cornea of chicken infected by Rous sarcoma virus. Many other experiments indicated that lysozyme had some relationship to the inhibition of tumor diffusion (1988 Clin. Expl. Metastasis 6:245–253; 1998 Folia Onclo 10, Suppl A: 219–224; 1988 Eur. J. Cancer Clin. Onco. 124:1737–1743). It is also found that lysozyme interacts with phospho- and glucolipid molecule of tumor cells. The lysozyme's inhibition effect on human tumor was reported. Laterza successfully cured a case of small intestine reticulation sarcoma with diffusion after operation and radiotherapy ("Atti del II Simposium Internazionale sul Lisozima", Milano. 7–8–9 1961. Vol I, sez V, pp 49–50). Battaglia et al. found that, though lysozyme could not reduce the volume of tumor, it had distinct effects of pain-killing and helping recovery in curing carcinomas of stomach, prostate, uterus and mammary gland ("Atti del II Simposium Internaionale sul Lisozima di Fleming", Milano. 34–5 1964. Vol I, sez IV, pp 69–76). In Japan, the application of lysozyme in curing cancer was patented (1980 Jpn Kokai Tokkyo Koho 33, 409; 1980 Jpn Kokai Tokkyo Koho 33,408). Besides, A. Vacca et al. in 1985 reported an attempt of curing multiple myeloma by chemoimmunology with oral lysozyme as an immunomodulating agent. Their experiments indicated that 50% of the patients treated with a large amount of lysozyme had improved immune ability as compared with the controls (Chemiother IV n.2:147–155,1985). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

EXAMPLE 3

Expression of LYC4 in E. coli

The cDNA sequence encoding LYC4 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TTGCGGATCCATGAAGGCATCCGTGGTTC-3' (SEQ ID NO:5).

This primer contained a cleavage site of restriction endonuclease BamH I, followed by 19 nucleotides of LYC4 coding sequence starting from the start codon.

The sequence of 3'-end primer was:

5'-GTTCGTCGACCTACAGCTTGCAACCATCC-3' (SEQ ID NO:6).

This primer contains a cleavage site of restriction endonuclease SalI, a translation terminator and partial LYC4 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance (Amp'), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform E.coli M15/rep4 (Qiagen) containing multi-copy of plasmid pREP4 which expressed repressor of lacI and was resistant to kanamycin (Kan'). Transformants were screened out in LB medium containing Amp and Kan. The positive clones of transformant were cultured overnight in LB liquid medium supplemented with Amp (100 ug/ml) and Kan (25 ug/ml). The plasmids were extracted. The size and direction of the inserted fragments were verified by HindIII digestion. The sequencing confirmed that LYC4 cDNA fragment was correctly inserted into the vector.

The overnight culture was 1:100–1:250 diluted, inoculated into large volume medium, and cultured until the 600 nm optical density ($OD_{600}$) reached 0.4–0.6. IPTG (isopropylthio-beta-D-galactoside) was added to final concentration of 1 mM. By deactivating repressor of LacI, IPTG induced and promoted P/O, thereby increasing the expression of gene. The cells were cultured for another 3–4 hours, and then centrifuged (6000×g, 20 mins). The inclusions were sonicated, and cell was collected and precipitates was solved in 6M guanidine hydrochloride. After clarification, the dissolved LYC4 in solution were purified by nickel-chelated column chromatography under the conditions suitable for the tight binding of 6-His tagged protein and column. LYC4 was eluted with 6M-guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column, and then eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was 16 kDa, as identified by 12% SDS-PAGE.

Moreover, the sequencing results of the 10 amino acids at the N- and C-terminal of the expressed protein indicated that they were identical to those in SEQ ID NO:4.

EXAMPLE 4

Expression of LYC4 in Eukaryotic Cells (CHO Cell Line)

In this example, the cDNA sequence encoding LYC4 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TTGCAAGCTTATGAAGGCATCCGTGGTTC-3' (SEQ ID NO:7),

This primer contained a cleavage site of restriction endonuclease HindIII, followed by 20 nucleotides of LYC4 coding sequence starting from the start codon.

The sequence of 3'-end primer was:

5'-GTTCGGATCCCTACAGCTTGCAACCATCC-3' (SEQ ID NO:8)

The primer contained a cleavage site of restriction endonuclease BamHI, a translation stop codon, and partial LYC4 coding sequence.

These cleavage sites of restriction endonuclease in primers corresponded to the cleavage sites in expression vector pcDNA3 for CHO cell. This vector encoded two kinds of antibiotic resistance (Amp' and Neo'), a phage replication origin (fl ori), a virus replication origin (SV40 ori), a T7 promoter, a virus promoter (P-CMV), a Sp6 promoter, a polyadenylation signal of SV40 and the corresponding poly A sequence thereof, a polyadenylation signal of BGH and the poly A sequence thereof.

The vector pcDNA3 and insertion fragment were digested with HindIII and BamHI, and linked together. Subsequently, E.coli strand DH5 α was transformed with linkage mixture. Transformants were screened out in LB medium containing Amp. The clones containing the needed constructs were cultured overnight in LB liquid medium supplemented with Amp (100 ug/ml). Plasmids were extracted. The sequencing indicated that LYC4 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the enzyme activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0–1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was 16 kDa as identified by 12% SDS-PAGE.

Moreover, the sequencing results of the 10 amino acids at the N- and C-terminal of the expressed protein indicated that they were identical to those in SEQ ID NO:4.

EXAMPLE 5

Antibody Preparation

Antibodies were produced by immunizing animals with the recombinant proteins obtained in the above examples. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of LYC4 gene in vitro.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated DNA molecule having a nucleotide sequence encoding a polypeptide having the amino acid sequence of amino acids 20–146 of SEQ ID NO:4.

2. The DNA molecule of claim 1 wherein said nucleotide sequence encodes a polypeptide having the amino acid sequence of SEQ ID NO:4.

3. The DNA molecule of claim 1 wherein said nucleotide sequence has the nucleotide sequence of nucleotides 179–619 of SEQ ID NO:3.

4. An isolated lysozyme polypeptide having the amino acid sequence of amino acids 20–146 of SEQ ID NO:4.

5. The polypeptide of claim 4 wherein said polypeptide has the amino acid sequence of SEQ ID NO:4.

6. A vector containing the DNA sequence of claim 1.

7. A host cell transformed by the vector of claim 6.

8. The host cell of claim 7 which is *E.coli*.

9. The host cell of claim 7 which is a eukaryotic cell.

10. A method for producing a LYC4 protein which comprises:

(a) introducing an expression vector for producing a LYC4 protein, said vector comprising a nucleotide sequence encoding a polypeptide having the amino acid sequence of amino acids 20–146 of SEQ ID NO:4, wherein said nucleotide sequence is operably linked to at least one expression control sequence, into a host cell, thereby forming a recombinant host cell;

(b) culturing the recombinant host cell of (a) under conditions suitable for expression of the DNA molecule encoding the polypeptide, such that LYC4 protein is produced; and (c) isolating the LYC4 protein so produced.

11. The method of claim 10 wherein said nucleotide sequence comprises nucleotides 179–619 of SEQ ID NO:3.

12. An isolated nucleotide molecule which is the antisense sequence of the DNA molecule of claim 1.

* * * * *